US010155067B2

(12) United States Patent
Persson et al.

(10) Patent No.: US 10,155,067 B2
(45) Date of Patent: Dec. 18, 2018

(54) FIBRE-BASED SURGICAL IMPLANT AND METHOD OF MANUFACTURE

(71) Applicant: INTERNATIONAL LIFE SCIENCES, LLC, Nashville, TN (US)

(72) Inventors: Anders Persson, Gothenburg (SE); Eugenio Ferrario, Gothenburg (SE)

(73) Assignee: International Life Sciences LLC, Marietta, GA (US)

( * ) Notice: Subject to any disclaimer, the term of this patent is extended or adjusted under 35 U.S.C. 154(b) by 0 days.

(21) Appl. No.: 15/250,327

(22) Filed: Aug. 29, 2016

(65) Prior Publication Data

US 2017/0049927 A1 Feb. 23, 2017

Related U.S. Application Data

(62) Division of application No. 12/863,242, filed as application No. PCT/SE2009/000016 on Jan. 16, 2009, now Pat. No. 9,427,494.

(30) Foreign Application Priority Data

Jan. 21, 2008 (SE) ...................................... 0800139

(51) Int. Cl.
*A61F 2/30* (2006.01)
*A61L 27/18* (2006.01)
(Continued)

(52) U.S. Cl.
CPC .......... *A61L 27/18* (2013.01); *A61F 2/30756* (2013.01); *A61L 27/50* (2013.01);
(Continued)

(58) Field of Classification Search
CPC ............................. A61F 2/30756; A61L 27/18
See application file for complete search history.

(56) References Cited

U.S. PATENT DOCUMENTS 3,317,924 A 5/1967 LeVeen ................................. 3/1
3,945,052 A 3/1976 Liebig .................................... 3/1
(Continued)

FOREIGN PATENT DOCUMENTS

EP 0 505 634 9/1992 ............ A61L 27/00
EP 1 351 630 3/2006 ............... A61F 2/30
(Continued)

OTHER PUBLICATIONS

International Search Report issued in a corresponding foreign application, PCT/SE2009/000016, pp. 1-7 (dated Jul. 30, 2009).
(Continued)

*Primary Examiner* — Zade Coley
*Assistant Examiner* — Olivia C Chang
(74) *Attorney, Agent, or Firm* — David G. Rosenbaum; Benjamin D. Rotman; Rosenbaum IP, P.C.

(57) ABSTRACT

A fiber-based surgical implant stabilized against fraying, includes a thermally crimped flat-knitted fabric of a biocompatible, optionally biodegradable, polymer material having a glass transition temperature or other thermally induced secondary conformational mobility threshold in the temperature range of from 20° C. to +170° C. Also disclosed is a corresponding fabric and methods of producing the implant and the fabric.

13 Claims, 8 Drawing Sheets

(51) Int. Cl.
  *A61L 27/58* (2006.01)
  *A61L 27/50* (2006.01)
  *D04B 21/16* (2006.01)
  *A61F 2/44* (2006.01)

(52) U.S. Cl.
  CPC .............. *A61L 27/58* (2013.01); *D04B 21/16* (2013.01); *A61F 2/3094* (2013.01); *A61F 2002/30008* (2013.01); *A61F 2002/30065* (2013.01); *A61F 2002/30077* (2013.01); *A61F 2002/3096* (2013.01); *A61F 2002/30172* (2013.01); *A61F 2002/30616* (2013.01); *A61F 2002/4495* (2013.01); *A61F 2210/0004* (2013.01); *A61F 2210/0066* (2013.01); *A61F 2210/0071* (2013.01); *A61F 2230/0052* (2013.01); *A61F 2250/0017* (2013.01); *D10B 2509/08* (2013.01)

(56) References Cited

U.S. PATENT DOCUMENTS

| | | | |
|---|---|---|---|
| 4,769,038 A | 9/1988 | Bendavid et al. | 623/13 |
| 5,004,474 A | 4/1991 | Fronk et al. | 623/13 |
| 5,733,335 A * | 3/1998 | Ishikawa | A61F 2/52 2/267 |
| 6,093,205 A | 7/2000 | McLeod et al. | 623/17 |
| 6,120,539 A | 9/2000 | Eldridge et al. | 623/11.11 |
| 7,037,342 B2 | 5/2006 | Nilsson et al. | 623/21.15 |
| 2003/0094019 A1 | 5/2003 | Miyake et al. | 66/195 |
| 2006/0058862 A1 | 3/2006 | Dong et al. | 623/1.5 |
| 2006/0271157 A1 | 11/2006 | Edens et al. | 623/1.13 |
| 2007/0055093 A1 | 3/2007 | Beraud | 600/30 |

FOREIGN PATENT DOCUMENTS

| | | | |
|---|---|---|---|
| GB | 892 980 | 4/1962 | |
| GB | 1 299 963 | 12/1972 | A61F 1/00 |
| WO | WO 1995/025550 | 9/1995 | A61L 27/00 |
| WO | WO 98/37813 | 9/1998 | A61B 17/00 |
| WO | WO 2002/054992 | 7/2002 | A61F 2/30 |

OTHER PUBLICATIONS

EP Extended Search Report and Search Opinion, EP Application No. 09704906.8, pp. 1-8 (dated Dec. 8, 2017).

* cited by examiner

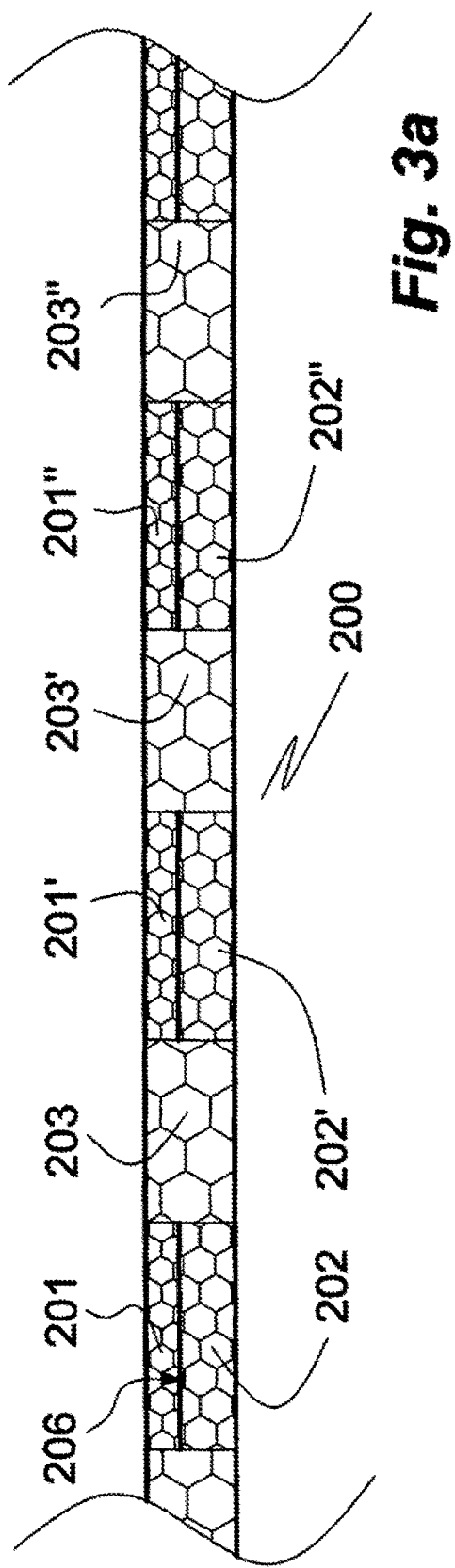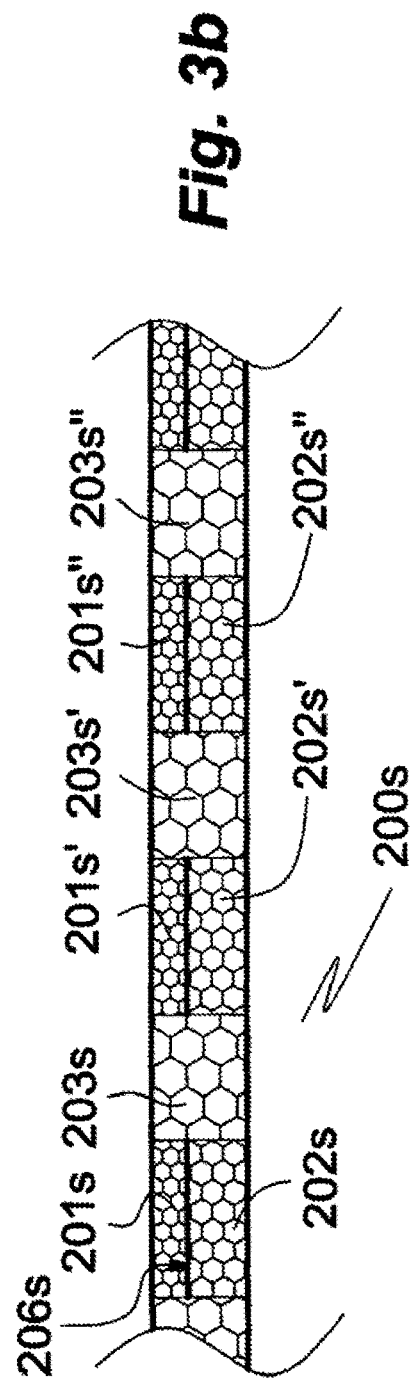

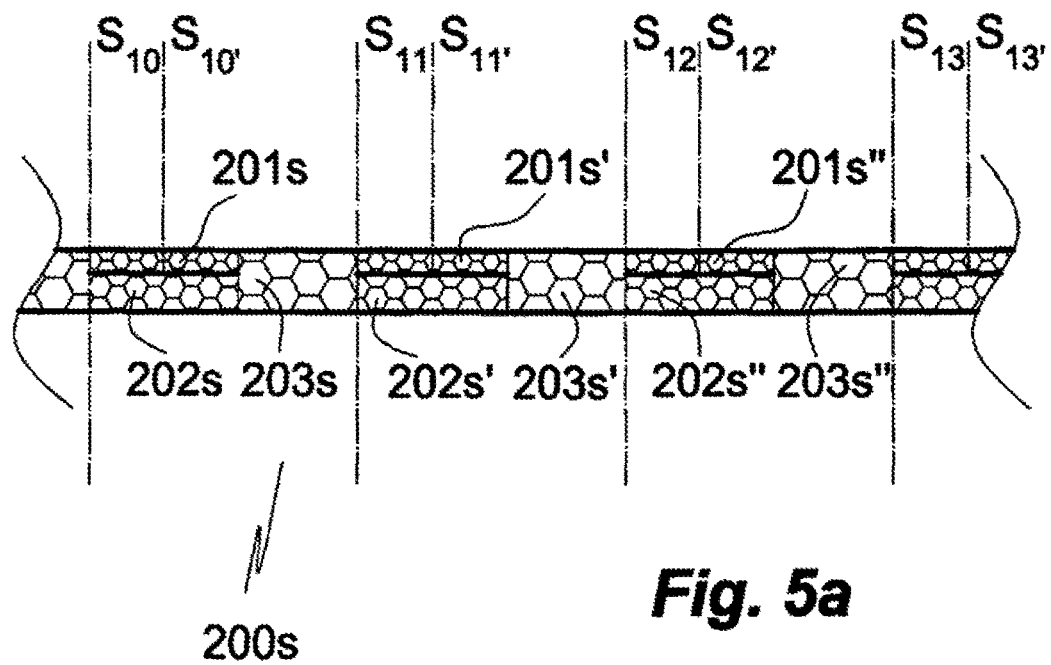
*Fig. 5a*
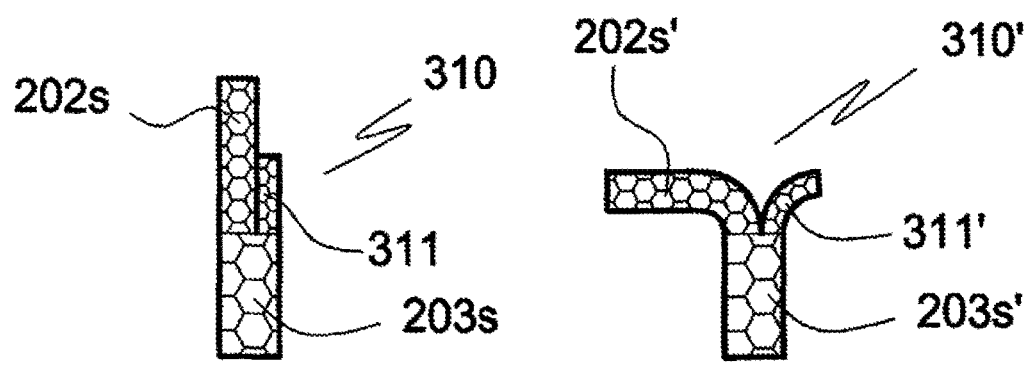
*Fig. 5*  *Fig. 5b*

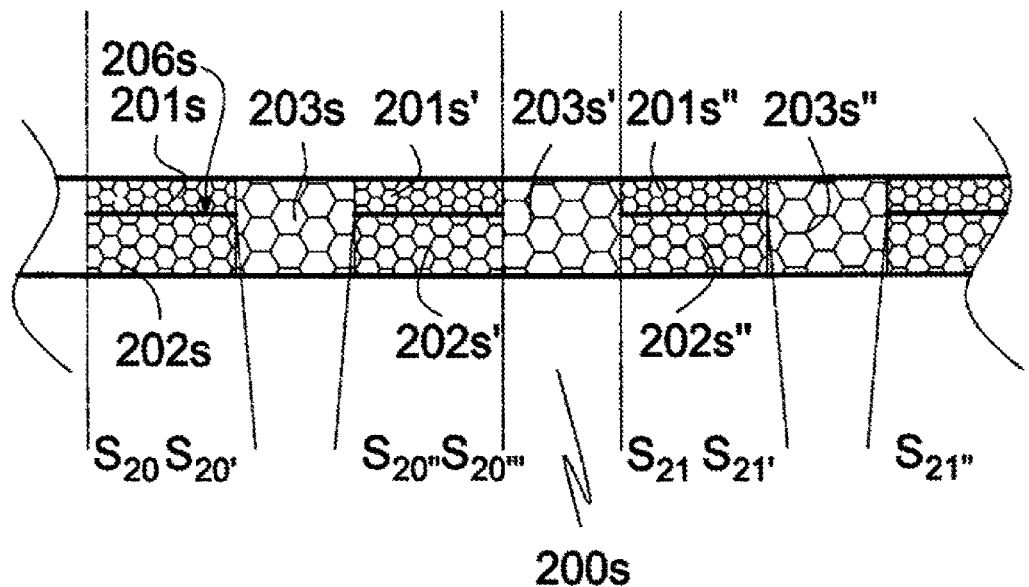
*Fig. 6a*
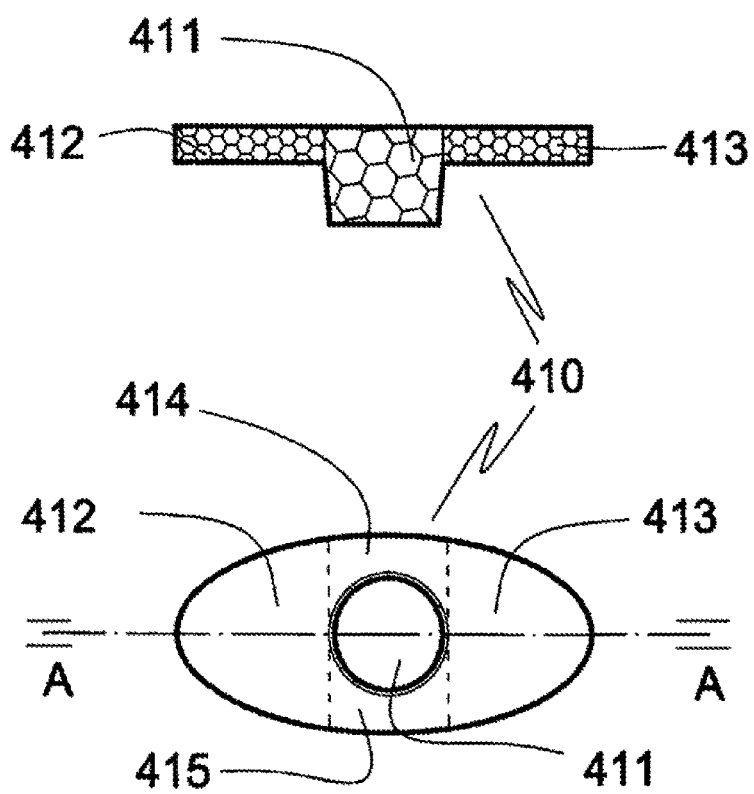
*Fig. 6*
*Fig. 6b*

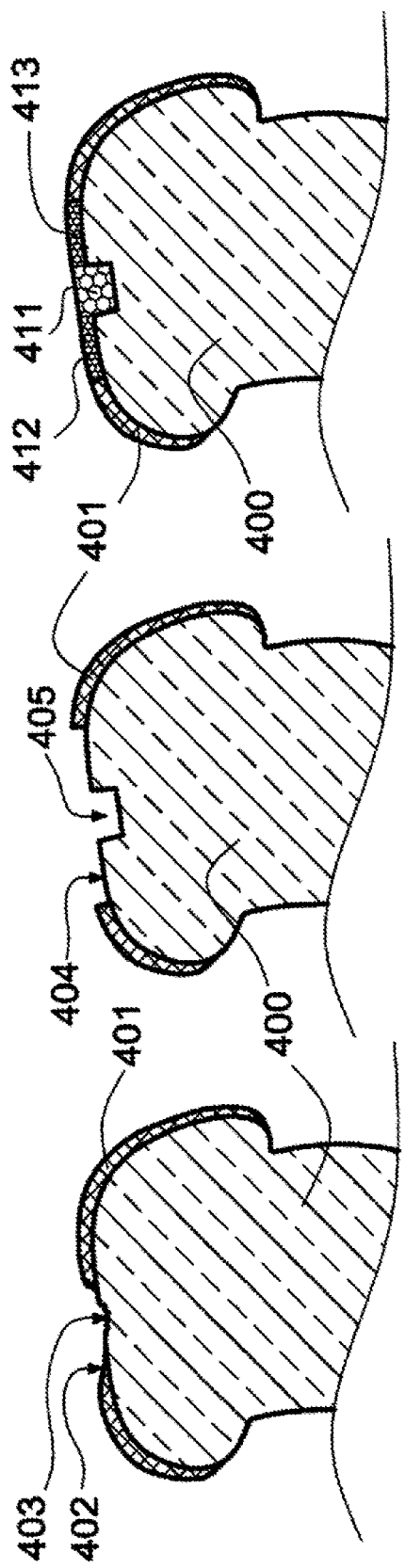

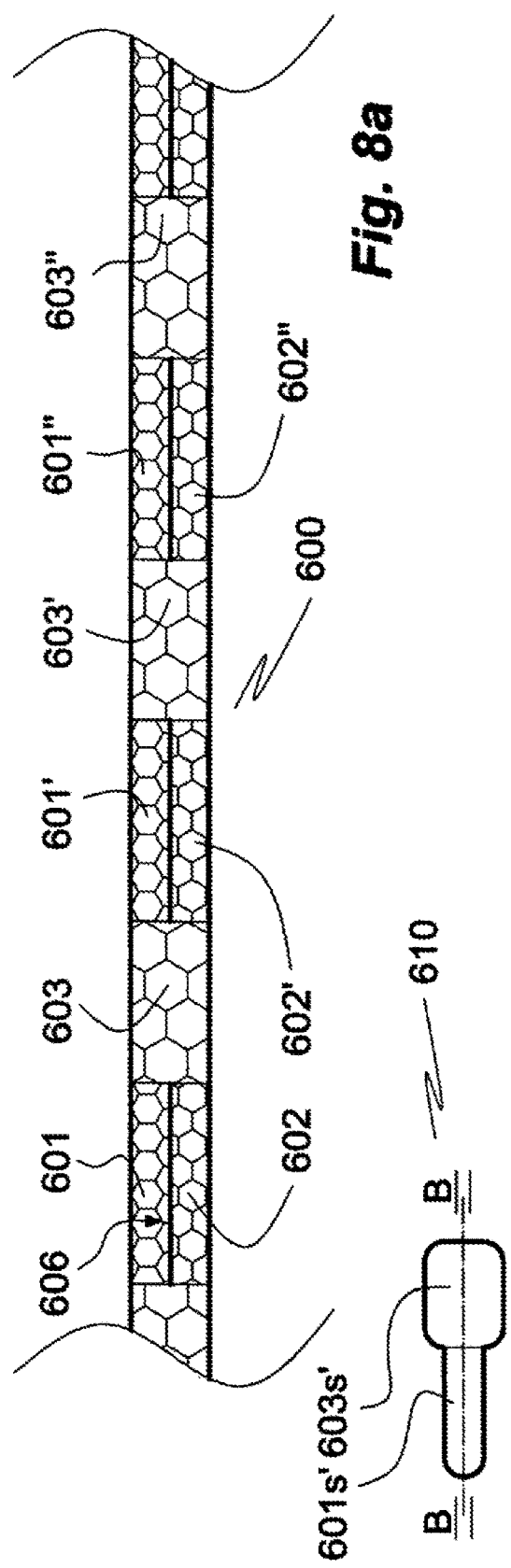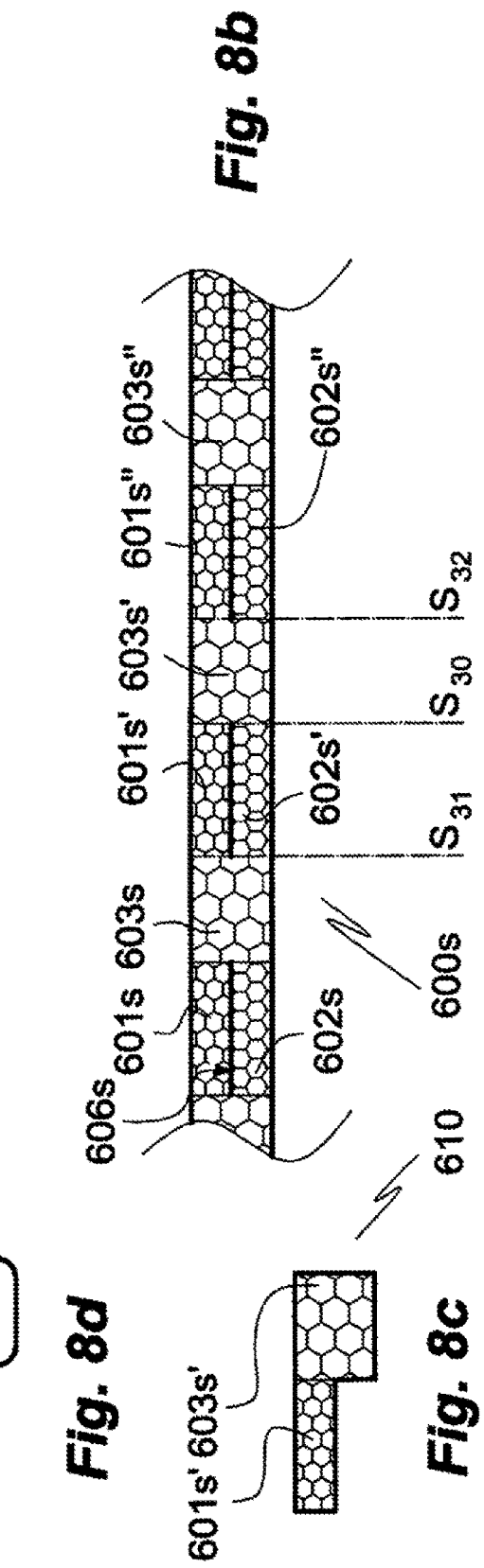

FIBRE-BASED SURGICAL IMPLANT AND METHOD OF MANUFACTURE

CROSS-REFERENCE TO RELATED APPLICATIONS

The present applications claims priority from and is a divisional of U.S. patent application Ser. No. 12/863,242, filed Sep. 16, 2010, which is a U.S. national phase application claiming priority to PCT Application No. PCT/SE2009/000016, filed Jan. 16, 2009; which claims priority from Swedish Patent Application No. SE 0800139-8, filed Jan. 21, 2008, all herein incorporated by reference in their entireties.

FIELD OF THE INVENTION

The present invention relates to a fibre-based surgical implant, a fabric for use in the manufacture of the implant, and methods for producing the fabric and the implant.

BACKGROUND OF THE INVENTION

A wide range of fibre-based surgical implants are known in the art. To be tolerated by the organism an implant has to be biocompatible. Certain uses additionally benefit from the implant being made of or comprising biodegradable material. Fibres for use in biocompatible implants are, in particular, made from suitable synthetic polymers. The fibres of an implant can be disposed in form of an ordered pattern, such as in a woven or knitted textile material, or in a non-ordered pattern, such as in a non-woven textile material. Surgical implants comprising knitted materials are disclosed, for instance, in U.S. Pat. No. 6,093,205 A, EP 505 634 B1, and EP 1 351 630 B1.

For economic reasons a textile fabric for use in implants would benefit from being manufactured in a size allowing the production of multiple implants or implant elements from it. The implants or elements for use in implants would have to be cut out from the fabric. Depending on the production method and textile pattern of the fabric, the degrees of cutting freedom may be restricted by the risk of compromising the integrity of the products by the textile material unraveling or fraying at cut edges. The problem may be aggravated by movements of tissue disposed adjacent to an implant in situ. A common fixation mode for textile implants is by suture(s) penetrating the implant near its fringe(s). Tearing by the suture(s) on implant is an important cause of fraying and of such implants losing their attachment to the respective bone or soft tissue. Fraying of an implanted textile material may cause a malign biological response of host tissue by mechanically induced inflammation and/or particle synovitis. In consequence the implant might require explanation. To avoid the risk of fraying woven fabrics for implant applications should not be cut along the warp. One commercially available woven fabric implant comprised by this restriction is the Artelon® TMC Spacer (Nilsson et al., J Hand Surg, 2005; 30A(2)380-9). Hence, the dimensions of a manufactured implant of this kind will have to be a compromise in view of the need to make an implant of given form and size fit as many patients as possible. Although a woven implant may be available in different sizes its case-by-case refined biometric and anatomic adaptation would be desirable. With a textile design that permits unrestricted cutting in the plane of the fabric a ready-made implant could be supplied with a shape better adapted to anatomical and biometric requirements. Even a final tailoring by the surgeon can be enabled during surgery. The need of adapting a ready-made implant to a patient is particularly pronounced if it is a part of an articular joint surface that needs treatment. In that case it is a definite benefit if the implant can be trimmed by the surgeon or assisting medical personnel. Fraying of a textile implant thus should be avoided by all means.

SUMMARY OF THE INVENTION

A thermally crimped flat-knitted fabric of a biocompatible, optionally biodegradable, material suitable for forming therefrom a surgical implant stabilized against fraying is disclosed, wherein the fabric comprises or consists of a polymer material having a glass transition temperature, in particular one of from 20° C. to 170° C., or another secondary thermally induced conformational mobility threshold within this range.

A method of producing a flat-knitted fabric for use in the manufacture of a surgical implant stabilized against fraying is disclosed and comprises: providing one or more fibres of a biocompatible, optionally biodegradable, polymer material having a glass transition temperature, in particular one of from 20° C. to 170° C., or other thermally induced secondary conformational mobility threshold within this range; knitting a flat fabric from the one or more fibres; crimping the fabric thermally.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 1a is top view of a transverse section a first embodiment of a flat-knitted poly(urethane urea) ribbon, enlarged;

FIG. 1b is a top view of a transverse section of the flat-knitted ribbon of FIG. 1a, after shrinking, enlarged;

FIGS. 1c to 1e are top views of standardized implant patches of comprised by a set of patches punched out from the flat-knitted ribbon of FIG. 1b, enlarged;

FIG. 3a is a partial view of a first embodiment of an interlaced double poly(urethane urea) flat-knitted ribbon of the invention comprising interlaced sections separated by non-interlaced sections, in a longitudinal section and enlarged;

FIG. 3b is the interlaced double flat-knitted ribbon of FIG. 3a, after shrinking and in the same enlarged view;

FIG. 4 b is an intraarticular spacer implant of the invention formed for implantation from the implant body of FIG. 4, in the same view;

FIG. 5 is a sectional view of another intraarticular spacer implant body of the invention excised from the flat-knitted ribbon of FIG. 3b, enlarged;

FIG. 5a is the double interlaced flat-knitted ribbon of FIG. 3b, in the same enlarged view, with cutting planes for excision of the implant of FIG. 5 indicated;

FIG. 5b is an intraarticular spacer implant of the invention formed for implantation from the implant body of FIG. 5, in the same view;

FIG. 6 is still another intraarticular implant of the invention excised from the flat-knitted ribbon of FIG. 3b, in a sectional view (A-A, FIG. 6b), enlarged;

FIG. 6a is the double flat-knitted ribbon of FIG. 3b, in the same enlarged view, with cutting planes for the excision of the implant of FIG. 6 indicated;

FIG. 6b is a top view of the implant of FIG. 6, enlarged;

FIG. 7a is the diseased head of a joint, in a sectional view, enlarged;

FIG. 7b is the joint head of FIG. 7 a prepared for implantation, in the view of FIG. 7a, enlarged;

FIG. 7c is the joint head of FIG. 7b, provided with the implant of FIG. 6, in the view of FIGS. 7a and 7b;

FIG. 8a is a partial view of a second embodiment of an interlaced double poly(urethane urea) flat-knitted ribbon of the invention, in a longitudinal section (B-B, FIG. 8d) and enlarged;

FIG. 8b is the interlaced double flat-knitted ribbon of FIG. 8a, after shrinking and in the same enlarged view, with cutting planes indicated;

FIG. 8c is an intraarticular spacer implant of the invention excised from the flat-knitted ribbon of FIG. 8b, in the same view and enlarged;

FIG. 8d is a top view of the spacer implant of FIG. 8c, enlarged.

DETAILED DESCRIPTION OF THE INVENTION

Figure 1:
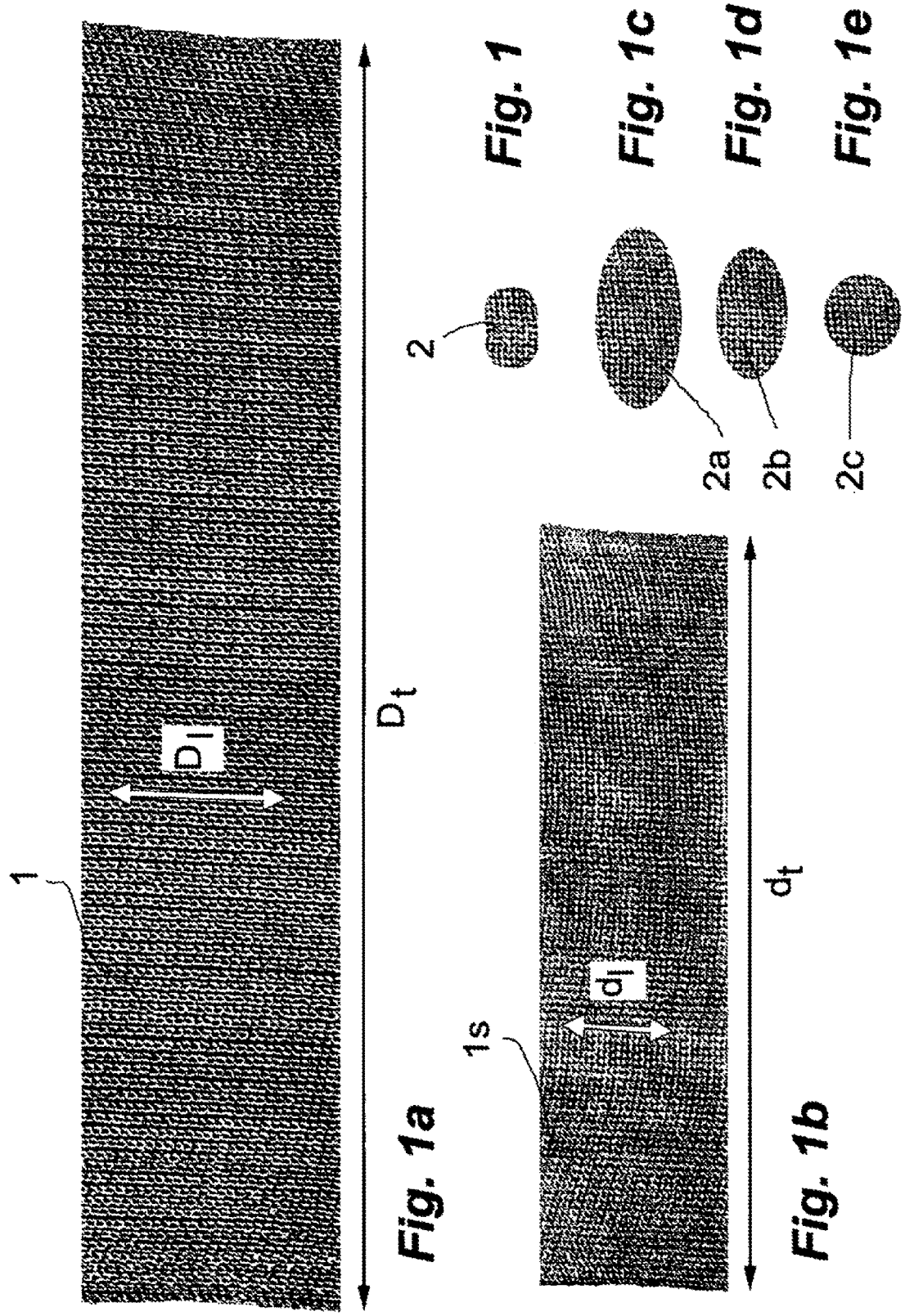
FIG. 1 is a top view of a first embodiment of the implant of the invention, excised from the shrunk flat-knitted ribbon of FIG. 1b or cut to size at bedside from the standardized implant patch of FIG. 1d, enlarged.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

An object of the invention is to provide a textile material of the aforementioned kind having little or no tendency to fray at cut edges thereof.

Another object of the invention is to provide a surgical implant comprising or consisting of such non-fraying textile material.

A further object of the invention is to provide methods of producing a non-fraying textile material and a corresponding implant.

Additional objects of the invention will become evident from the following summary of the invention, preferred embodiments thereof illustrated in a drawing, and the appended claims.

According to a first aspect of the present invention is disclosed fibre-based surgical implant of the aforementioned kind stabilized against fraying at a cut edge. The fibres of the implant are comprised by a flat-knitted fabric of a biocompatible, optionally biodegradable, polymer material. The polymer material is one capable of being thermally crimped. A measure of this capacity is that the polymer has a glass transition temperature, in particular one of from 20° C. to 170° C. However, there are also polymer materials that can be thermally crimped but do not exhibit a distinct glass transition temperature; within the same temperature range these materials do however exhibit at least one thermally induced conformational mobility threshold that is not a melting threshold, i.e. is a threshold of a secondary not a primary transition. One important polymer material of this kind is poly(urethane urea).

The implant of the invention may comprise fibres of more than one thermally shrinkable polymer material. The implant of the invention may also comprise fibres of varying thickness and/or fibre threads.

An optimal stabilizing effect is achieved by selecting polymer fibres that can be thermally crimped and a knitting pattern that makes the fibres interlock by their crimping action. The fabric may be crimped by, for instance, running it over heated roller(s). Crimping by means of heated cylindrical rollers will preserve the flatness of the fabric. Alternatively the fabric may be thermally crimped to give a non-flat form. This can be accomplished by, for instance, making the fabric abut a heated surface that is not flat, such as a heated concave metal surface. A fabric holder that negatively mirrors the geometry of the heated non-flat surface may be used to press the tissue gently against the heated surface to make the fabric adopt the form of the non-flat surface during the crimping process.

"Cut edge" is an edge formed by a cutting operation, such as by excision or punching. The cutting operation may be carried out in an automated fashion in the course of industrial production or manually at bedside by the use of a pair of scissors or a scalpel. The use of laser and particle beam cutting techniques is within the ambit of the invention.

"Knitted fabric" comprises any fabric manufactured by a knitting method, in particular by warp knitting, but does not comprise woven fabrics. Knitting methods useful in the invention are described, i.a., in: D J Spencer. Knitting technology, a comprehensive handbook and practical guide. Third edition, Woodhead Publishing Ltd., Cambridge 2001.

"Crimped knitted fabric" is a thermally crimped fabric. Useful crimping ranges according to the invention in a direction along the weft or perpendicular to the weft are from 10% to 70%, in particular from 25% to 60%, more particularly from 35% to 55%, most preferred about 45%. The thickness of the fabric of the invention is less affected by crimping than the width or length of the fabric, and may even increase as a result of crimping.

Useful polymer materials include poly(ortho ester), poly(glycolic acid), poly(lactic acid), poly(glycolic, lactic acid), poly($\beta$-hydroxybutyric acid), poly(imino carbonate), poly($\epsilon$-caprolactone), poly(glycolic/lactic acid, $\epsilon$-caprolactone), poly(ethyleneterephthalate), poly(etheretherketone), poly(urethane urea), polyurethane, polyamide. These useful materials are only given for exemplification. Thus any other biocompatible polymer having a glass transition temperature within the range given above may also be used.

According to a second aspect of the present invention is disclosed a thermally crimped flat knitted fabric of a biocompatible, optionally biodegradable, material. The material is suitable in the manufacture of non-fraying surgical implants by cutting techniques such as excision or punching. The fabric comprises or consists of a polymer material having an ordered domain, in particular a material having a glass transition temperature, in particular one of from 20° C. to 170° C., or a secondary thermally induced conformational mobility threshold within that temperature range.

According to a third aspect of the present invention is disclosed a method of producing a flat knitted fabric for use in the manufacture of a surgical implant stabilized against fraying, comprising: providing one or more fibres of a biocompatible, optionally biodegradable, polymer material having a glass transition temperature, in particular one of from 20° C. to 170° C., or a secondary thermally induced conformational mobility threshold within that range; knitting a flat fabric from the one or more fibres; crimping the fabric thermally. In particular, the method comprises: (a) knitting in parallel superimposed planes a first fabric ribbon and a second fabric ribbon to form a first fabric ribbon section and second fabric ribbon section; (b) interlacing the fibres used in forming said first and second ribbon sections over a selected ribbon length to knit an interlaced ribbon section; repeating steps (a) and (b) for a selected number of times so as to provide an interlaced fabric ribbon comprising a multitude of alternating double ribbon and interlacing ribbon sections.

According to a fourth aspect of the present invention is disclosed a method of producing a surgical implant stabilized against fraying comprising: providing the product of the method of producing a flat-knitted fabric for use in the manufacture of a surgical implant stabilized against fraying; forming the implant from the fabric, in particular by cutting.

According to a fifth aspect of the present invention is disclosed an intraarticular spacer substantially consisting of a crimped flat-knitted fabric of polymer material.

According to a sixth aspect of the present invention is disclosed an intraarticular spacer excised from a crimped flat-knitted fabric of polymer material.

According to a seventh aspect of the present invention is disclosed a flat-knitted fabric obtained or obtainable by the method of the invention.

According to an eight aspect of the present invention is disclosed a surgical implant obtained or obtainable by the method of the invention.

It is within the ambit of the present invention to provide the fabric of the invention or an implant manufactured from the fabric with agents that improve or safeguard its incorporation into living tissue, such as with hormones, in particular growth hormones, antibiotics, cartilage constituents, including cultured cartilage cells, etc. Such agents are well known to the person skilled in the art and need not to be detailed here.

The invention will now be explained in more detail by reference to a number of preferred embodiments illustrated in a drawing. FIGS. 1-1e are photographic views. The other figures are roughly drawn sketches; in the sectional views the thickness of knitted fabric and of implants produced from knitted shrunk fabric is grossly exaggerated for reasons of clarity.

Example 1

Shrunk flat-knitted poly(urethane urea) ribbon. Yarn: 13 Tex poly(urethane urea) (Artelon®, Artimplant AB, Göteborg, Sweden). Equipment: Comez DNB/EL-800 (Comez s.p.A., Cilavegna, Italy) double needle bed crochet machine, for the production of technical and medical articles. Machine specifications: 15 gauge, 6 weft bars, double needle bed, latch needles. Heat set unit: Comez HSD/800 comprising 2 heat-set cylinders.

Figure 2:
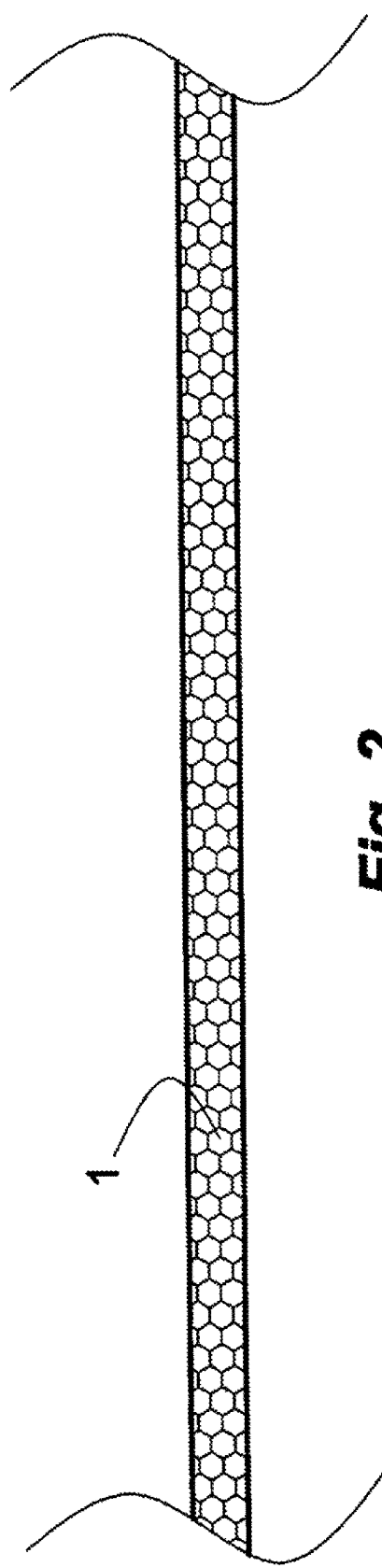
FIG. 2 is a partial view of the flat-knitted ribbon of FIG. 1a, in a longitudinal section and enlarged.
Figure 2A:
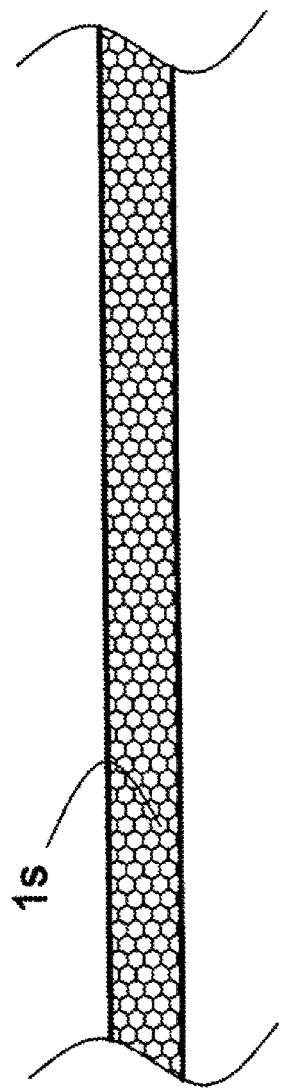
FIG. 2a is a partial view of the flat-knitted ribbon of FIG. 1b, after shrinking; in the same view as that of FIG. 2, enlarged.

A plain ribbon 1 of 14 cm width was knit in the machine (FIG. 1a, 2). The ribbon 1 was shrunk in the heat set unit at 130° C. to produce a shrunk ribbon 1b a thickness of 0.8 mm (FIGS. 1b, 2a). Process parameters: Knitting speed: 26 cm/min; heat set unit speed: 14 cm/min; shrinkage along warp: about 45% (cf DI, width of ribbon 1 and dI, width of ribbon 1 s); shrinkage across warp: about 45% (cf Dt, 20 loops, and dt, 20 loops). Warp thickness is slightly increased by shrinking. The warp knitting pattern is shown in Table 1. It is a sequence of four steps with 12 loops/cm.

By using the same parameters and knitting pattern a quadrupled thread gives a shrunk fabric of about 2.0 mm thickness.

TABLE 1

Warp knitting pattern of tricot ribbon

| Loop row | Binding device movement | | | | | | Loops/cm | Alimentation device setting (warp feed) | | | |
|---|---|---|---|---|---|---|---|---|---|---|---|
| | 2 | | 4 | | 5 | | | | | | |
| 1 | 2 | 2 | 3 | 3 | 2 | 2 | 12.00 | 1490 | 2610 | 1790 | 1450 |
| 2 | 2 | 1 | 2 | 1 | 2 | 3 | 12.00 | 1490 | 2610 | 1790 | 1450 |
| 3 | 1 | 1 | 3 | 3 | 2 | 2 | 12.00 | 1490 | 2610 | 1790 | 1450 |
| 4 | 1 | 2 | 4 | 5 | 2 | 1 | 12.00 | 1490 | 2610 | 1790 | 1450 |
| 5 | 2 | 2 | 3 | 3 | 2 | 2 | 12.00 | 1490 | 2610 | 1790 | 1450 |
| 6 | 2 | 1 | 2 | 1 | 2 | 3 | 12.00 | 1490 | 2610 | 1790 | 1450 |
| 7 | 1 | 1 | 3 | 3 | 2 | 2 | 12.00 | 1490 | 2610 | 1790 | 1450 |
| 8 | 1 | 2 | 4 | 5 | 2 | 1 | 12.00 | 1490 | 2610 | 1790 | 1450 |

Example 2

Formation and implantation of an articular head spacer implant from the shrunk flat-knitted poly(urethane urea) ribbon of Example 1. An articular implant 2 is excised from the ribbon 1 s at bedside. In implantation the implant 2 is disposed, for instance, on the articular head of a proximal interphalangeal joint. The implant 2 is be affixed to the bone by suturing or stapling.

For convenience of handling, a set of implant bodies of varying size and/or form, such as the set 2a, 2b, 2c illustrated in FIGS. 1c-1e, can be provided to the medical profession. The availability of the set allows the physician to select an implant body of suitable size and/or form, and to trim it to make it fit the particular purpose. Implants of standardized size and form that need not to be trimmed can also be provided as single items or in form of sets.

Example 3

Shrunk flat-knitted double interlaced poly(urethane urea) ribbon. Yarn: 13 Tex poly(urethane urea) (Artelon®, Artimplant AB, Göteborg, Sweden). Equipment: Comez DNB/EL-800 (Comez s.p.A., Cilavegna, Italy) double needle bed crochet machine, for the production of technical and medical articles. Machine specifications: 15 gauge, 6 weft bars, double needle bed, latch needles. Heat set unit: Comez HSD/800 comprising 2 heat-set cylinders.

A ribbon 200 of two parallel warp knitted layers was knit, a front layer 201, 201', 201", etc. of a thickness of about 1.0 mm, and a rear layer 202, 202', 202", etc., of a thickness of about 1.6 mm. The layers 201, 201', 201"; 202, 202', 202" interlace over sections 203, 203', 203", etc. separated by the non-interlaced sections disposed equidistantly along the ribbon 200 (FIG. 3a). The ribbon 200 is shrunk in the heat set unit to form a shrunk ribbon 200 s, in which the elements of the non-shrunk ribbon retain their reference numbers followed by "s" (FIG. 3b). Process parameters: Knitting speed: 26 cm/min; heat set unit speed: 14 cm/min; shrinkage along warp: about 45%; shrinkage across warp: about 45%. Reference numbers 206, 206 s indicate separation between non-interlaced sections.

A ribbon 200 of two parallel warp knitted layers was knit, a front layer 201, 201', 201", etc. of a thickness of about 1.0 mm, and a rear layer 202, 202', 202", etc., of a thickness of about 1.6 mm. The layers 201, 201', 201"; 202, 202', 202" interlace over sections 203, 203', 203", etc. separated by the non-interlaced sections disposed equidistantly along the ribbon 200 (FIG. 3a). The ribbon 200 is shrunk in the heat set unit to form a shrunk ribbon 200s, in which the elements of the non-shrunk ribbon retain their reference numbers followed by "s" (FIG. 3b). Process parameters: Knitting speed: 26 cm/min; heat set unit speed: 14 cm/min; shrinkage along warp: about 45%; shrinkage across warp: about 45%. Reference numbers 206, 206s indicate separation between non-interlaced sections.

Example 4

Figure 4A:
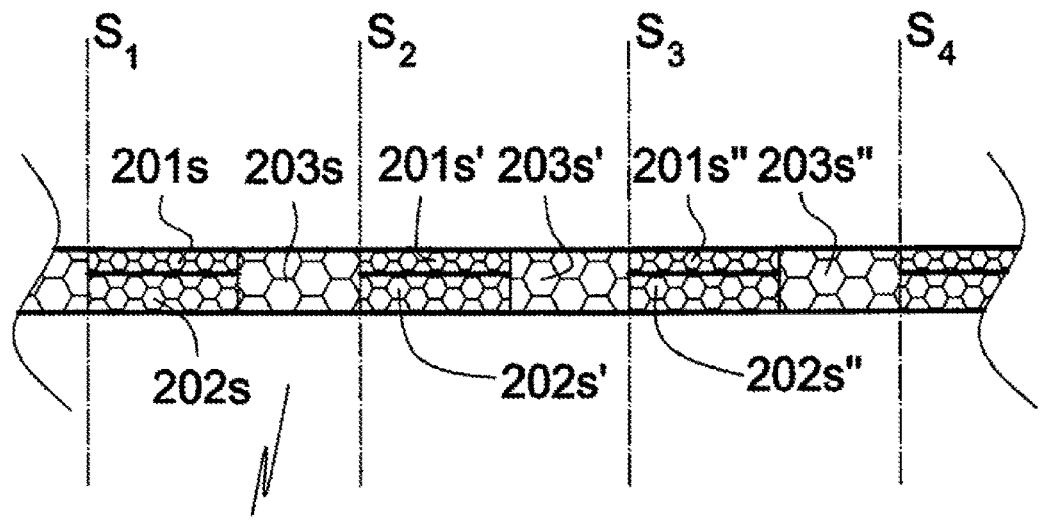
FIG. 4a is the double interlaced flat-knitted ribbon of FIG. 3b, in the same enlarged view, with cutting planes for the excision of the implant of FIG. 4 indicated.
Figures 4, 4B:
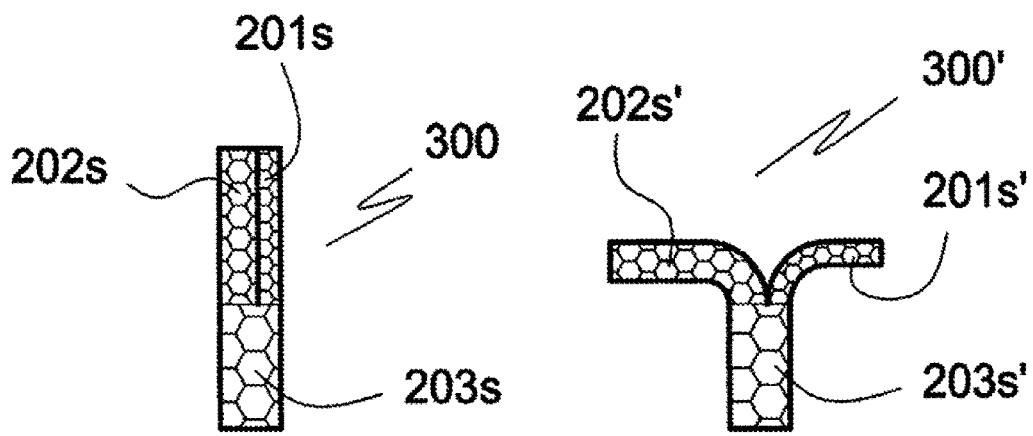
FIG. 4 is a sectional view of an intraarticular spacer implant body of the invention cut out from the flat-knitted ribbon of FIG. 3b, enlarged.
Figure 4C:
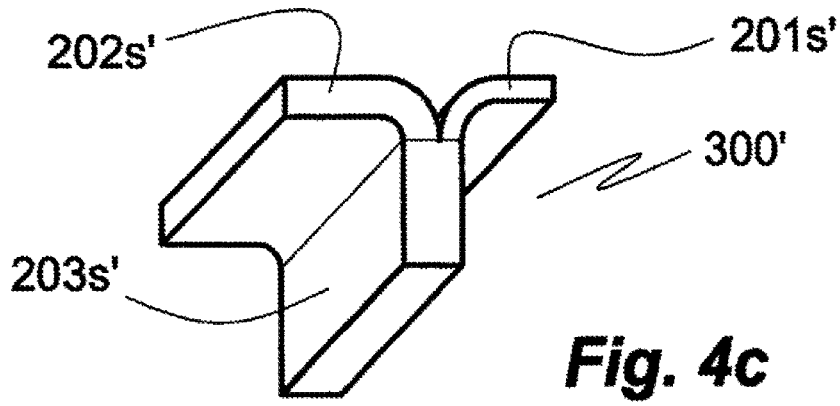
FIG. 4c is a representation of the implant of FIG. 4 in a perspective view.

Formation and implantation of a first articular spacer from the shrunk flat-knitted poly(urethane urea) double interlaced ribbon of Example 3. Implant bodies 300, etc. of identical size and shape, each comprising an interlacing section, 203s, 203s', 203s" and a pair of adjoining non-interlacing sections, that is a top section 201s, 202s'; 201s". and a bottom section 202s, 202s', 202s" are cut out from the shrunk interlaced ribbon 200s along cutting planes $S_1$, $S_2$, $S_3$, $S_4$ (FIG. 4a). Bending away the non-interlaced sections 201s, 202s of the implant body 300 in opposite directions results in a T-formed articular spacer 300' (FIGS. 4b, 4c) of the general geometric kind disclosed in FIG. 1 of U.S. Pat. No. 7,037, 342 B2. Intra-articular implantation of the spacer 300' and fixation is accomplished in a manner substantially corresponding to that disclosed for the known T-formed spacer of U.S. Pat. No. 7,037,342 B2.

Example 5

Formation and implantation of a second articular spacer from the shrunk flat-knitted poly(urethane urea) double interlaced ribbon of Example 3. Implant bodies 310 (FIG. 5), etc. of identical size and shape, each comprising an interlacing section, 203s, 203s', 203s", etc. and a pair of adjoining non-interlacing sections, that is a top section 311s, etc. and a bottom section 202s, 202s', 202s", etc. are cut out from the shrunk ribbon 200 s along cutting lines $S_{10}$, $S_{10'}$, $S_{11}$, $S_{11'}$, $S_{12}$, $S_{12'}$, $S_{13}$, $S_{13'}$, etc. (FIG. 5a). Bending away the non-interlaced sections 201s, 202s of the implant body 310 in opposite directions results in a T-formed articular spacer 310' (FIG. 5b) of the general geometric kind disclosed in FIG. 1 of U.S. Pat. No. 7,037,342 B2. Intra-articular implantation of the spacer 310' and fixation is accomplished in a manner substantially corresponding to that disclosed for the known T-formed spacer of U.S. Pat. No. 7,037,342 B2.

Example 6

Formation and implantation of a third articular spacer from the shrunk flat-knitted poly(urethane urea) double interlaced ribbon of Example 3. Implant bodies 410 (FIGS. 6, 6b) of identical size and shape, each comprising wings, 412, 413 extending diametrically opposite from a central body 411 are cut out from the shrunk ribbon 200s along cutting lines $S_{20}$, $S_{20'}$, $S_{20''}$, $S_{20'''}$; $S_{21}$, $S_{21'}$, $S_{21''}$, $S_{21'''}$, etc. (FIG. 6a). In addition, material of the interlaced portion extending from the central body 411 in a transverse direction (in respect of the ribbon 200s) has to be removed (cut off) to bring the thickness of portions 414, 415 formed from section 203s to that of the wings 412, 413, which are formed from non-interlaced portions 201s, 201s'.

Implantation of the implant 410 on a head 400 of a joint is illustrated in FIGS. 7a-7c. The central portion of the head 400 is diseased. Some surface areas 402 are entirely lacking cartilage 401 or their cartilage layer is compromised. In addition the subchondral bone of a central area is affected (FIG. 7a). The bone 400 is prepared for implantation by removing diseased cartilage and bone. A shallow depression 405 in the bone 400 in form of the frustrum of a cone is scooped out to remove the diseased bone tissue. The depth and form of the depression 405 matches the portion of the implant's central body 411 extending from the wings 412, 413 towards the smaller circular end face of the central body 411. This portion of the implant 411 is inserted into the depression 405. One flat side of the flexible wings 411, 412 is now in abutment with a bone surface from which diseased cartilage has been removed. The implant 410 is fastened on the bone 400 by biocompatible glue, optionally in combination suturing to adjacent cartilage.

Example 7

Shrunk flat-knitted double interlaced poly(urethane urea) ribbon. Yarn: 13 Tex poly(urethane urea) (Artelon®, Artimplant AB, Göteborg, Sweden). Equipment: Comez DNB/EL-800 (Comez s.p.A., Cilavegna, Italy) double needle bed crochet machine, for the production of technical and medical articles. Machine specifications: 15 gauge, 6 guide bars, double needle bed, latch needles. Heat set unit: Comez HSD/800 comprising 2 heat-set cylinders.

A ribbon 600 of two parallel warp knitted layers was knit, a front layer 601, 601', 601", etc. of a thickness of about 1 mm, and a rear layer 602, 602', 602", etc. of same thickness. The layers 601, 601', 601"; 602, 602', 602" interlace over sections 603, 603', 603", etc. separated by the non-interlaced sections disposed equidistantly along the ribbon 600 (FIG. 8a). The ribbon 600 is shrunk in the heat set unit to form a shrunk ribbon 600 s, in which the elements of the non-shrunk ribbon retain their reference numbers followed by "s". Process parameters: Knitting speed: 18/22 cm/min; heat set unit speed: 10/12 cm/min; shrinkage along warp: about 45%; shrinkage across warp: about 45%. The warp knitting pattern is shown in Table 2. It is a sequence of 120 steps with 8.5 loops/cm for the interlace and 10 loops/cm for the non-interlaced sections. Four guide bars were employed to produce the ribbon 600 shown in FIG. 8a.

invention, and including such departures from the present disclosure as, within the known and customary practice within the art to which the invention pertains.

What is claimed is:

1. A musculo-skeletal surgical implant consisting at least one flat-knit warp patterned layer of biocompatible polymer material having either a glass transition temperature or at least one thermally induced conformational mobility threshold that is not a melting threshold, within a temperature ranging from 20° C. to 170° C., wherein the biocompatible polymer material is heat shrunk and configured not to fray when cut along a warp of the at least one flat-knit layer of biocompatible polymer material when the biocompatible polymer material is at its glass transition state or thermally induced conformational mobility threshold.

2. The implant of claim 1, wherein the glass transition temperature or the temperature of a thermally induced conformational mobility threshold is from 35° C. to 120° C.

3. The implant of claim 1, wherein the fabric is heat shrunk by 10 percent or more in length or width in at least one direction along a length or width of the fabric.

4. The implant of claim 1, wherein the polymer material comprises ester, urethane, urea and/or amide bonds.

5. The implant of claim 4, wherein the polymer material is selected from poly(ortho ester), poly(glycolic acid), poly (lactic acid), poly(glycolic, lactic acid), poly(glycolic/lactic acid, ε-caprolactone), poly(β-hydroxybutyric acid), poly (imino carbonate), poly(ε-caprolactone), poly(ethyleneterephthalate), poly(etheretherketone), polyurea, poly(urethane urea), polyurethane, polyamide.

6. The implant of claim 4, wherein the polymer material is selected from polyester, polyurethane, polyurethane urea, polyamide, polyurea.

7. The implant of claim 1, wherein at least a second flat-knit warp patterned layer is bonded to the at least one flat-knit warp patterned layer through interlacing.

8. The implant of claim 7, further comprising one or more sections wherein the at least one flat-knit warp layer is bonded to the at least second flat-knit warp pattered layer

TABLE 2

| Warp knitting pattern of interlaced ribbon | | | | | | | | | | | |
|---|---|---|---|---|---|---|---|---|---|---|---|
| Loop row | Binding device movement | | | | | | | Loops/ cm | Alimentation device setting (warp feed) | | |
| | 2 | | 4 | 5 | | 7 | | | | | |
| 1 | 2 | 2 | 2 | 2 | 2 | 3 | 2 | 1 | 8.50 | 2050 | 2300 | 2050 |
| 2 | 2 | 1 | 2 | 3 | 2 | 2 | 1 | 1 | 8.50 | 2050 | 2300 | 2050 |
| 3 | 1 | 1 | 2 | 2 | 2 | 1 | 1 | 2 | 8.50 | 2050 | 2300 | 2050 |
| 4 | 1 | 2 | 2 | 1 | 2 | 2 | 2 | 2 | 8.50 | 2050 | 2300 | 2050 |
| 5-56 | | | | | | | | | 13x [1-4] | | | |
| 57 | 2 | 2 | 2 | 2 | 2 | 3 | 2 | 1 | 8.50 | 2050 | 2300 | 2050 |
| 58 | 2 | 1 | 2 | 3 | 2 | 2 | 1 | 1 | 8.50 | 2050 | 2300 | 2050 |
| 59 | 1 | 1 | 3 | 2 | 2 | 2 | 1 | 2 | 10.00 | 1850 | 2300 | 1850 |
| 60 | 1 | 2 | 2 | 2 | 2 | 1 | 2 | 2 | 10.00 | 1850 | 2300 | 1850 |
| 61 | 2 | 2 | 2 | 1 | 2 | 2 | 2 | 1 | 10.00 | 1850 | 2300 | 1850 |
| 62 | 2 | 1 | 2 | 2 | 2 | 3 | 1 | 1 | 10.00 | 1850 | 2300 | 1850 |
| 63 | 1 | 1 | 2 | 3 | 2 | 2 | 1 | 2 | 10.00 | 1850 | 2300 | 1850 |
| 64 | 1 | 2 | 2 | 2 | 2 | 1 | 2 | 2 | 10.00 | 1850 | 2300 | 1850 |
| 65-120 | | | | | | | | | 14x [61-65] | | | |

While the invention has been described in connection with various embodiments, it will be understood that the invention is capable of further modifications. This application is intended to cover any variations, uses or adaptations of the invention following, in general, the principles of the and one or more sections wherein the at least one flat-knit warp layer is not bonded to the at least second flat-knit warp pattered layer.

9. The implant of claim 8, wherein a bonded section extends over two or more rows of meshes.

10. The implant of claim 8, wherein a non-bonded section extends over two or more rows of meshes.

11. The implant of claim 1, wherein the polymer material is in a glass transition state and stabilizes the fabric to reduce fraying.

12. The implant of claim 1, wherein the fabric is configured to shrink both along the warp and across the warp when exposed to the glass transition temperature of the polymer material.

13. The implant of claim 1, wherein the fabric is configured to shrink by at least about 45% along the warp and the fabric is heat shrunk by at least about 45% across the warp when exposed to the glass transition temperature of the polymer material.

\* \* \* \* \*